(12) United States Patent
Thomas (10) Patent No.: US 11,241,552 B2
(45) Date of Patent: Feb. 8, 2022

(54) OROPHARYNGEAL AIRWAY DEVICE

(71) Applicant: Nicole Thomas, Orlando, FL (US)

(72) Inventor: Nicole Thomas, Orlando, FL (US)

( * ) Notice: Subject to any disclaimer, the term of this patent is extended or adjusted under 35 U.S.C. 154(b) by 315 days.

(21) Appl. No.: 16/293,063

(22) Filed: Mar. 5, 2019

(65) Prior Publication Data

US 2020/0282164 A1  Sep. 10, 2020

(51) Int. Cl.
*A61M 16/04* (2006.01)
*A61M 16/00* (2006.01)
*A61M 16/06* (2006.01)

(52) U.S. Cl.
CPC ...... *A61M 16/049* (2014.02); *A61M 16/0003* (2014.02); *A61M 16/0431* (2014.02); *A61M 16/0666* (2013.01); *A61M 2202/0208* (2013.01)

(58) Field of Classification Search
CPC ............ A61M 16/049; A61M 16/0003; A61M 16/0666; A61M 16/0431; A61M 16/0463; A61M 16/0495; A61M 2202/0208
See application file for complete search history.

(56) References Cited

U.S. PATENT DOCUMENTS

| | | | |
|---|---|---|---|
| 4,068,785 A * | 1/1978 | Goudreau ............ | A63B 47/001 224/247 |
| 4,369,991 A * | 1/1983 | Linder ............... | A61M 16/0463 285/148.26 |
| 4,744,358 A | 5/1988 | McGinnis | |
| 6,098,617 A | 8/2000 | Connell | |
| 8,220,461 B1 * | 7/2012 | Guerra ............. | A61M 16/0488 128/207.14 |
| 8,485,194 B2 * | 7/2013 | Guerra ............. | A61M 16/0493 128/207.14 |
| 2003/0094809 A1 * | 5/2003 | Inoue .................. | F16L 37/0987 285/93 |
| 2007/0267025 A1 | 11/2007 | Lyons et al. | |
| 2010/0186749 A1 * | 7/2010 | Macan ............... | B29C 66/1122 128/207.15 |
| 2013/0014754 A1 * | 1/2013 | Guerra ............. | A61M 16/0493 128/202.16 |
| 2013/0239970 A1 * | 9/2013 | Pizzini ............. | A61M 16/0666 128/205.22 |
| 2016/0029923 A1 | 2/2016 | Ozenne | |

(Continued)

OTHER PUBLICATIONS https://commons.wikimedia.org/wiki/File:Cantilever_Snap-fit.gif, Feb. 17, 2012 (Year: 2012).*

(Continued)

*Primary Examiner* — Douglas Kay
(74) *Attorney, Agent, or Firm* — Allen, Dyer, Doppelt + Gilchrist PA (57) ABSTRACT

An oropharyngeal airway device includes an elongated hollow body having proximal and distal ends, and a collar secured to the proximal end of the elongated hollow body. The device also includes an aspiration tube and an adapter where the adapter has a first open end and an opposing second open end. The first and second open ends are each coupled to the aspiration tube. In addition, the device includes a delivery conduit coupled to the adapter and positioned within the elongated hollow body in order to deliver gas from a gas supply to the distal end of the elongated hollow body and into an airway of a patient. The device includes at least one fastener within the collar for removably securing the adapter to the collar.

18 Claims, 6 Drawing Sheets

(56) References Cited

U.S. PATENT DOCUMENTS

2017/0333154 A1* 11/2017 LeBeau ............... A61B 90/39
2020/0179632 A1*  6/2020 Worley ............ A61M 16/0666
2021/0093818 A1*  4/2021 Shantha ................ A61B 5/06

OTHER PUBLICATIONS

L. Torossian and D. Bourell, "Experimental study of snap-fits using additive manufacturing", 26th Annual International Solid Freeform Fabrication 'SFF' Symposium, Austin, TX, 2015, pp. 1794-1803 (Year: 2015).*

* cited by examiner

OROPHARYNGEAL AIRWAY DEVICE

TECHNICAL FIELD

The present disclosure relates to the field of oral airway devices for patients, and, more particularly, to an oropharyngeal airway device.

BACKGROUND

An oropharyngeal airway is generally in the form of a Guedel airway. The Guedel airway is most often formed by a plastic tube comprised of three parts. A first main part is curved in order to follow the shape of the patient's oral cavity to the pharynx. The plastic tube maintains an unobstructed airway for the patient. Accordingly, the patient can breathe without the tongue obstructing the patient's airway, in particular when the patient is unconscious. A second part is comprised of rigid material and is placed between the patient's teeth. The rigidity prevents the patient from obstructing the airway by biting. A third part comprises a collar which rests on the patient's lips and keeps the tube from sliding further into the patient's mouth.

However, there is a need that has long existed for an improved oropharyngeal airway device.

SUMMARY

When a patient becomes unconscious, the muscles in their jaw relax causing the tongue to obstruct the patient's airway and prevent the patient from breathing. Generally, an oropharyngeal airway is used to maintain an unconscious patient's airway by preventing the tongue from obstructing the airway. However, often times the patient may need oxygen in addition to the use of an oropharyngeal airway. The typical oropharyngeal airway does not provide for providing oxygen, for example, to the patient so that a separate tracheal tube is required. Thus, an improved oropharyngeal airway device is disclosed that is adaptable to easily and quickly provide oxygen to a patient using a readily available nasal cannula and without a separate tracheal tube. In addition, a shortcoming of using a separate nasal cannula to the nose with an oropharyngeal airway is that oxygen could be delivered in the nose, but if the patient was exhaling through the oropharyngeal airway then measuring the carbon dioxide level was not possible. Accordingly, the present device is able to deliver oxygen and also measure carbon dioxide levels using the nasal cannula.

The device includes an elongated hollow body having proximal and distal ends, a collar secured to the proximal end of the elongated hollow body, and an adapter having a first open end and an opposing second open end. The first and second open ends of the adapter are each configured to accept an aspiration tube from a nasal cannula therein in order to convert the nasal cannula for use as an oropharyngeal cannula. In addition, the device includes at least one fastener within the collar that is configured to be used to removably secure the adapter to the collar.

The oropharyngeal airway device also includes a delivery conduit coupled to the adapter and positioned within the elongated hollow body in order to deliver a gas to the distal end of the elongated hollow body and into an airway of the patient. The elongated hollow body has a curved portion between the proximal end and the distal end.

In a particular aspect, the at least one fastener of the device may comprise a top arcuate half and a bottom arcuate half each extending from the collar towards each other and defining a slit configured for the aspiration tube to removably slide through and be secured between the top and bottom arcuate halves.

In another aspect, the at least one fastener may comprise a first piece extending from the collar and having a retaining lip at a distal end of the first piece. The adapter may have a second piece extending therefrom and having a complementary retaining lip configured to removably snap together with the retaining lip of the at least one fastener.

In yet another aspect, the at least one fastener may comprise a retaining slot within the collar, and where the adapter comprises a first piece extending in a first direction, and having a second piece extending perpendicular to the first piece in a second direction, and having a retaining lip at a distal end of the second piece being configured to removably slide into the retaining slot.

The delivery conduit of the oropharyngeal airway device may be in fluid communication with a gas supply in order to provide a gas, such as oxygen, to the patient.

DETAILED DESCRIPTION

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout.

Oropharyngeal airways come in a variety of sizes, from infant to adult, and are used commonly in pre-hospital emergency care and for short term airway management post anaesthetic or when manual methods are inadequate to maintain an open airway. Oropharyngeal airways are typically only used in unconscious patients, because of the likelihood that the device would stimulate a gag reflex in conscious or semi-conscious patients. This could result in vomit and potentially lead to an obstructed airway. Nasopharyngeal airways are mostly used instead as they do not stimulate a gag reflex. In general, oropharyngeal airways need to be sized and inserted correctly to maximize effectiveness and minimize possible complications, such as oral trauma.

In addition, the typical oropharyngeal airway does not provide for providing oxygen, for example, to the patient so that a separate tracheal tube is required. Thus, an improved oropharyngeal airway device is disclosed that is adaptable to easily and quickly provide oxygen to a patient using a readily available nasal cannula and without a separate tracheal tube. In addition, the present device is able to deliver oxygen and also measure carbon dioxide levels using the nasal cannula.

Figure 1:
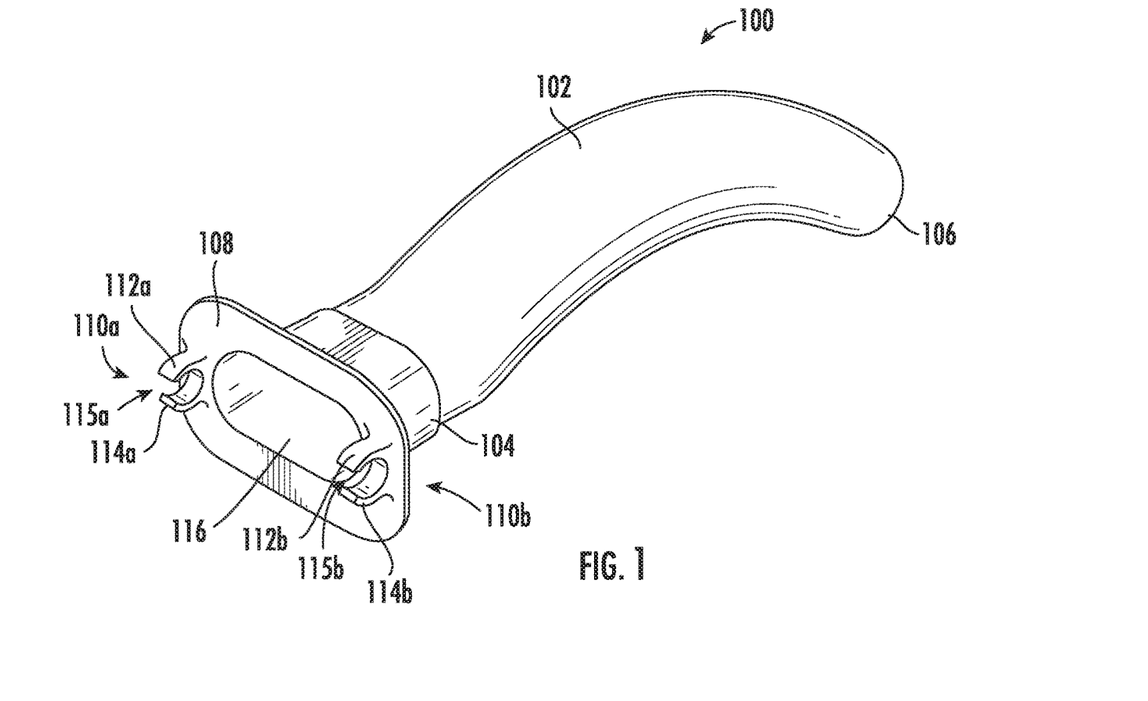
FIG. 1 is a schematic perspective view of an oropharyngeal airway device according to the present invention shown without an aspiration tube for clarity.

Referring now to FIG. 1, an oropharyngeal airway device 100 according to the present disclosure is now described. The oropharyngeal airway device 100 includes an elongated hollow body 102 having proximal 104 and distal ends 106. A collar 108 is secured to the proximal end 104 of the elongated hollow body 102. The elongated hollow body 102 has a curved portion between the proximal end 104 and the distal end 106. In addition, the device 100 includes at least one fastener within the collar 108 that is configured to be used to removably secure the adapter to the collar 108. In a particular aspect, there are two fasteners on the collar 108, with one fastener on each side of an opening 116 of the device 100.

A first fastener 110a includes a first top arcuate half 112a and a first bottom arcuate half 114a that each extend from the collar 108 towards each other and define a first slit 115a in order form the first fastener. On an opposing side of the collar 108, a second fastener 110b is similar to the first fastener 110a and includes a second top arcuate half 112b and a second bottom arcuate half 114b that each extend from the collar 108 towards each other and define a second slit 115b in order to form the second fastener 110b. The first and second fasteners 110a, 110b are configured for an aspiration tube to removably slide through the slits 115a, 115b and be secured between the respective top arcuate halves 112a, 112b and the bottom arcuate halves 114a, 114b as shown in FIG. 2.

Figure 2:
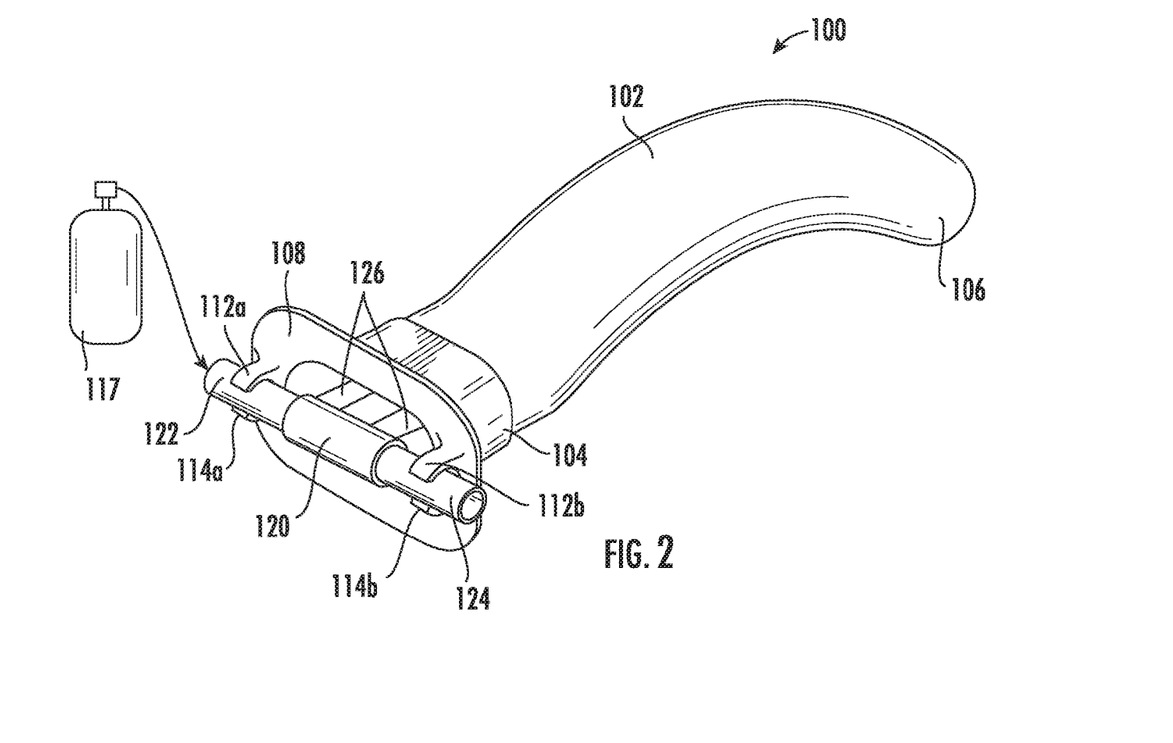
FIG. 2 is a schematic perspective view of the oropharyngeal airway device of FIG. 1 with the aspiration tube.

Referring now to FIG. 2, an adapter 120 is hollow and has a first end of an aspiration tube 122 coupled to a first open end and has a second end of the aspiration tube 124 coupled to an opposing second open end of the adapter 120. The adapter 120 is configured to accept the ends of the aspiration tube 122, 124 from a nasal cannula in order to easily convert the nasal cannula for use as an oropharyngeal cannula for an unconscious patient. As explained above, the device 100 includes that the first and second fasteners 110a, 110b within the collar 108 are configured to be used to removably secure the adapter 120 to the collar 108.

The oropharyngeal airway device 100 also includes a delivery conduit 126 coupled to the adapter 120 and positioned within the elongated hollow body 102 in order to deliver a gas to the distal end 106 of the elongated hollow body 102 and into an airway of the patient. The elongated hollow body 102 has a curved portion between the proximal end 104 and the distal end 106. The delivery conduit 126 may be in fluid communication with a gas supply 117 in order to provide a gas, such as oxygen, to the patient.

Figure 3:
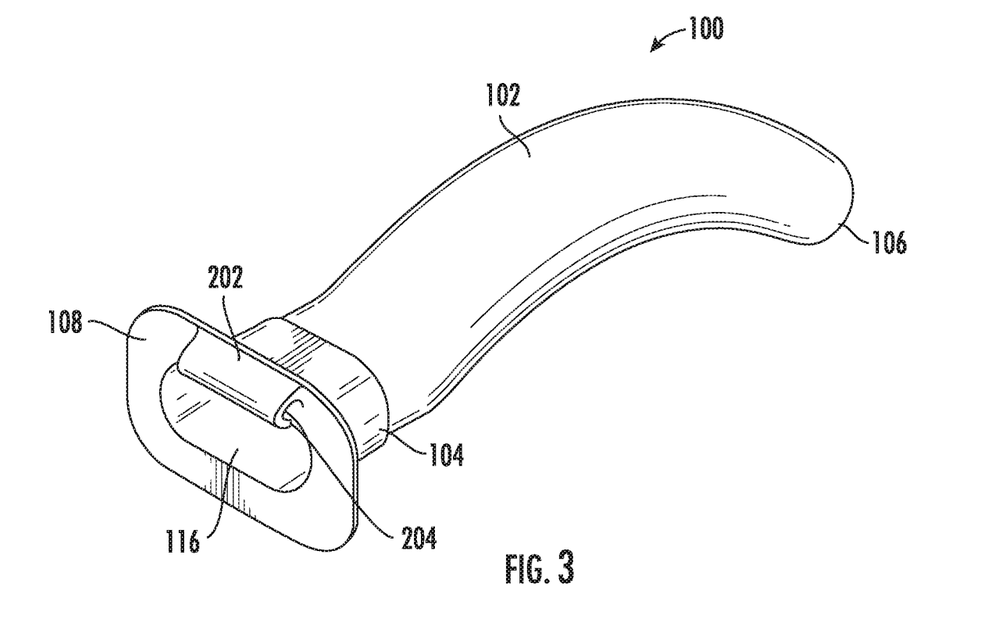
FIG. 3 is a schematic perspective view of another aspect of the oropharyngeal airway device according to the present invention shown without the aspiration tube for clarity.
Figure 4:
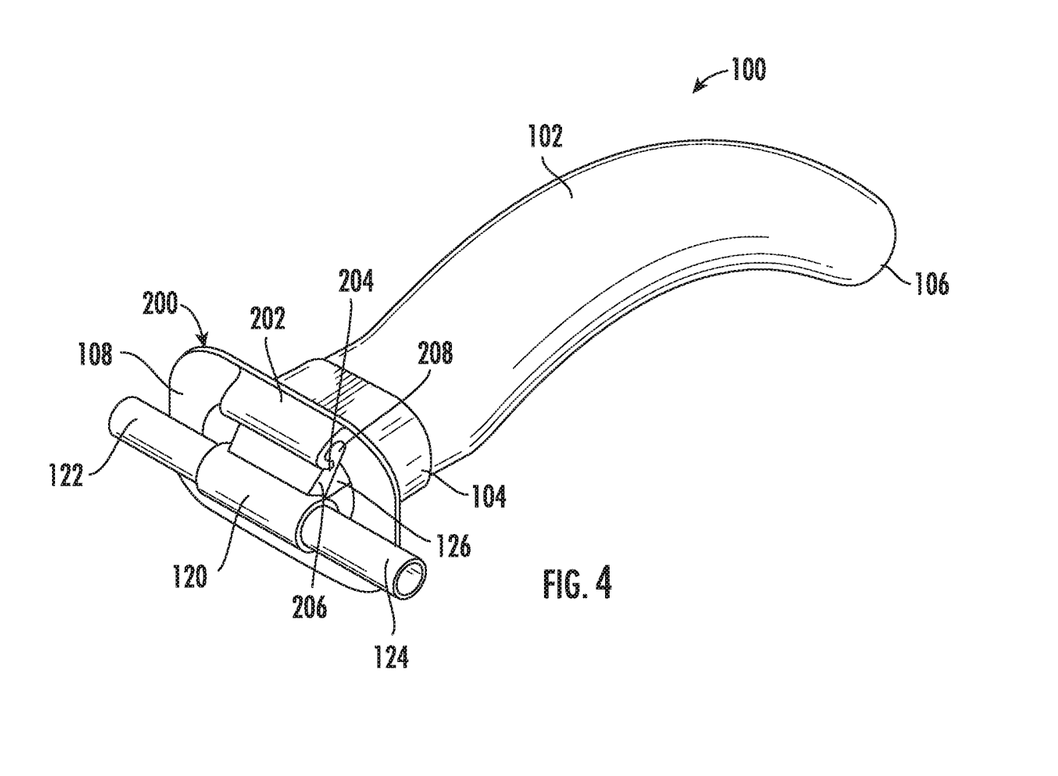
FIG. 4 is a schematic perspective view of the oropharyngeal airway device of FIG. 3 with the aspiration tube.

In another aspect as shown in FIGS. 3 and 4, a fastener 200 includes a first piece 202 extending from the collar 108 and having a retaining lip 204 at a distal end of the first piece 202. As shown in FIG. 4 with the adapter 120 coupled to the collar 108, the adapter 120 may have a second piece 206 extending therefrom and having a complementary retaining lip 208 configured to removably snap together with the retaining lip 204 of the fastener 200.

Figure 5:
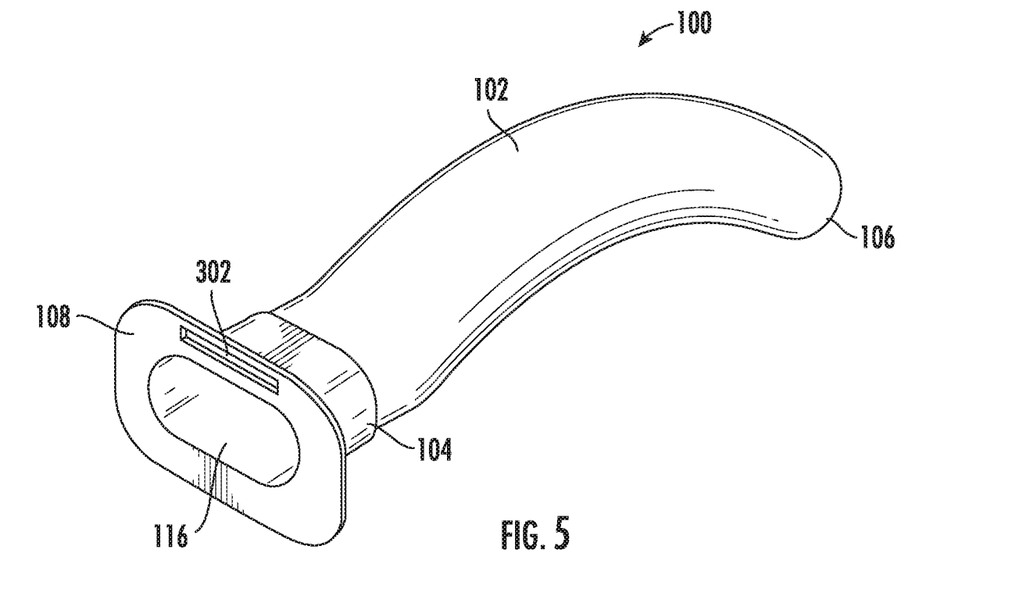
FIG. 5 is a schematic perspective view of yet another aspect of the oropharyngeal airway device according to the present invention shown without the aspiration tube for clarity.
Figure 6:
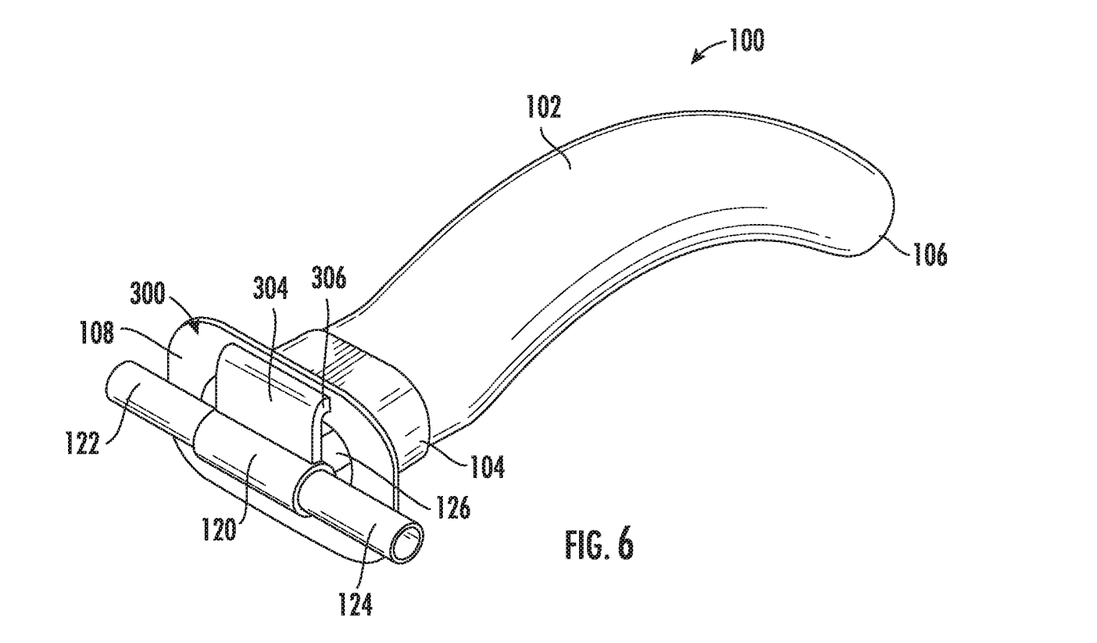
FIG. 6 is a schematic perspective view of the oropharyngeal airway device of FIG. 5 with the aspiration tube.

Referring now to FIGS. 5 and 6 of yet another aspect, a fastener 300 may comprise a retaining slot 302 within the collar 108. The adapter 120 shown in FIG. 6 comprises a first piece 304 extending in a first direction, and having a second piece 306 extending perpendicular to the first piece 304 in a second direction. A retaining lip 308 (see FIGS. 17 and 18) is positioned at a distal end of the second piece 306 and is configured to removably slide into the retaining slot 302 as shown in FIG. 6.

Figures 7, 7A:
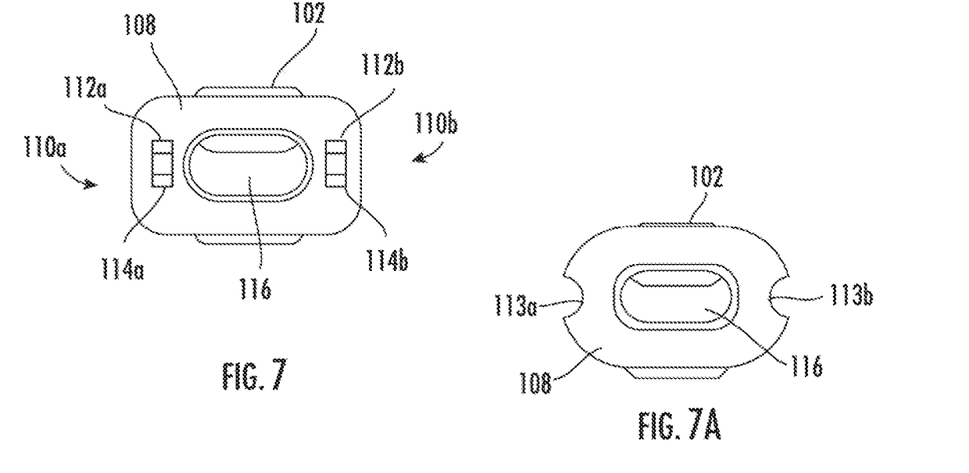
FIG. 7 is a schematic front view of the oropharyngeal airway device of FIG. 1 without the aspiration tube.
FIG. 7a is a schematic front view of another aspect of the oropharyngeal airway device for securing the aspiration tube.
Figure 8:
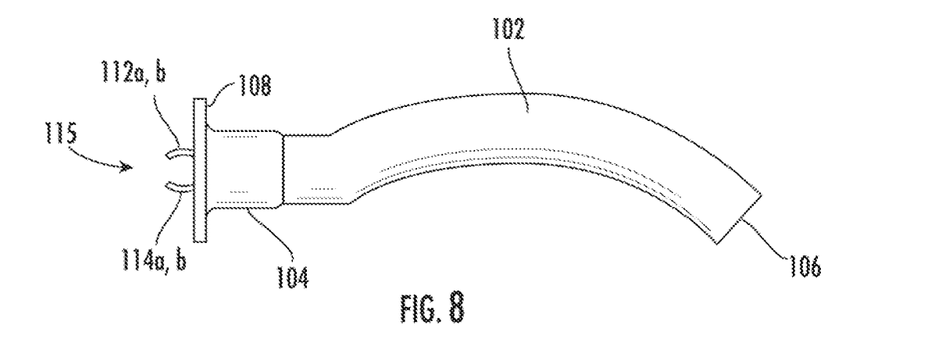
FIG. 8 is a schematic side view of the oropharyngeal airway device of FIG. 1 without the aspiration tube.

Referring now to FIGS. 7 and 8, front and side schematic views of the oropharyngeal airway device 100 are shown without the aspiration tube 122, 124 and adapter 120 for clarity. As described above, a collar 108 has a pair of fasteners 110a, 110b that are used to secure the aspiration tube 122, 124. The fasteners 110a, 110b are sized and positioned to hold an aspiration tube from a typical nasal cannula used in the medical field. Accordingly, nasal prongs (i.e. the "delivery conduit 126") of the nasal cannula will easily slide into the opening 116 in order to direct oxygen down the elongated hollow tube 102 and into the patient's airway. The elongated hollow body 102 includes a curved portion that is compatible with insertion into a patient's oral cavity and airway.

Another aspect of the oropharyngeal airway device 100 for securing the first and second ends of the aspiration tube 122, 124 is shown in FIG. 7a. In particular, cut outs 113a, 113b in the collar 108 are for holding the respective first and second ends of the aspiration tube 122, 124 on each side of the collar 108. This serves to position the delivery conduit 126 within the elongated hollow body 102 in order to deliver a gas to the distal end 106 of the elongated hollow body 102 and into an airway of the patient.

Figure 9:
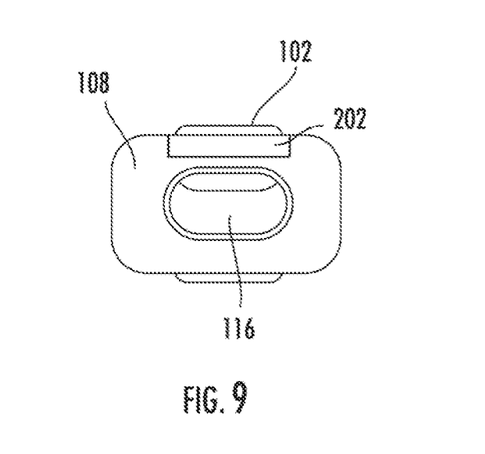
FIG. 9 is a schematic front view of the oropharyngeal airway device of FIG. 3 without the aspiration tube.
Figure 10:
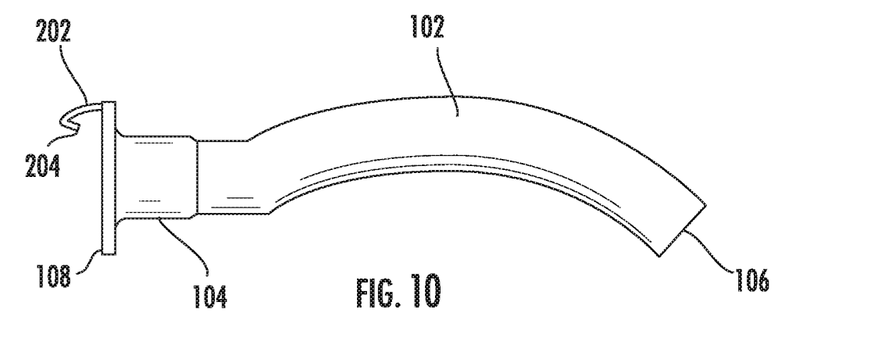
FIG. 10 is a schematic side view of the oropharyngeal airway device of FIG. 3 without the aspiration tube.

As shown in FIGS. 9 and 10 and in another particular aspect, a first piece 202 extends from the collar 108 and has a retaining lip 204 at a distal end. This provides for a second piece 206 that extends from the adapter 120, which also has a complementary retaining lip 208, to be removably snapped together with the retaining lip 204 of the fastener 200 as better viewed in FIG. 4 and described above.

Figure 11:
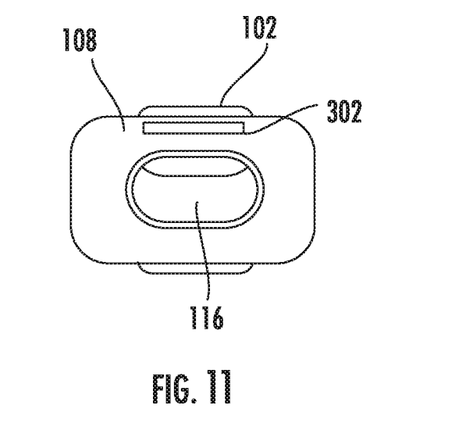
FIG. 11 is a schematic front view of the aspiration tube of the oropharyngeal airway device of FIG. 5 without the aspiration tube.
Figure 12:
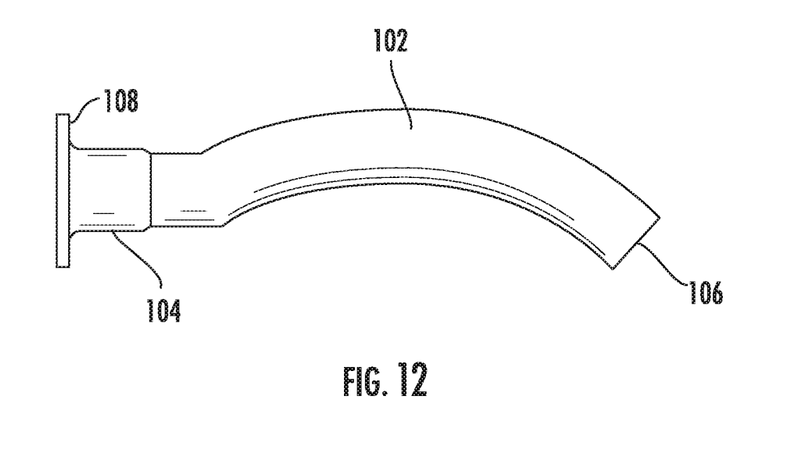
FIG. 12 is a schematic side view of the oropharyngeal airway device of FIG. 5 without the aspiration tube.

Referring now to FIGS. 11 and 12, in yet another aspect a retaining slot 302 is formed within the collar 108. The retaining slot 302 is configured to receive a retaining lip 308 (see FIGS. 17 and 18) of the adapter 120 so that the retaining lip 308 can removably slide into the retaining slot 302 as shown in FIG. 6 and effectively hold the aspiration tube 122, 124 and delivery conduit 126 in place.

Figure 13:
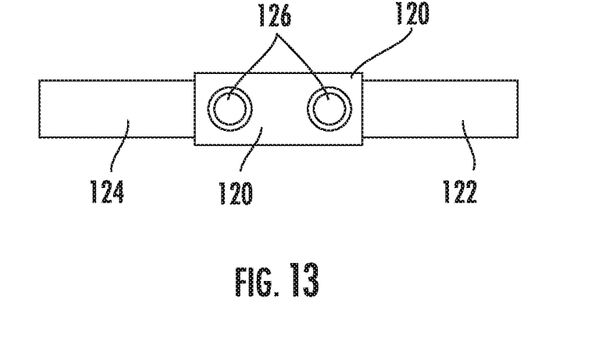
FIG. 13 is a schematic front view of the aspiration tube of the oropharyngeal airway device of FIG. 1.
Figure 14:
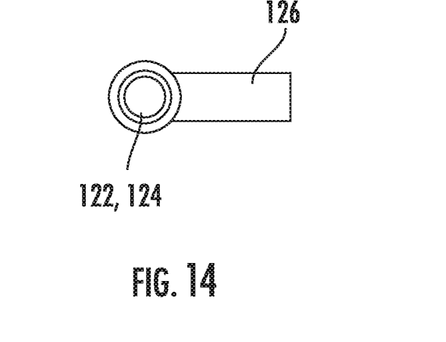
FIG. 14 is a schematic side view of the aspiration tube of the oropharyngeal airway device of FIG. 1.

The aspiration tube 122, 124 is shown in FIGS. 13-18 secured to the adapter 120. As shown in FIGS. 13 and 14, the adapter 120 is a typical nasal cannula having two nasal prongs 126 used to typically deliver oxygen to a patient. As described above with reference to FIGS. 1 and 2, in a particular aspect the collar 108 includes a pair of fasteners 110a, 110b that are used to hold and secure the aspiration tube 122, 124 so that the nasal cannula can be easily converted to an oropharyngeal airway device 100 if the patient is (or becomes) unconscious. Likewise, if a patient gains consciousness and the oropharyngeal airway is no longer required, the oropharyngeal airway device 100 can be converted back to the nasal cannula.

Figure 15:
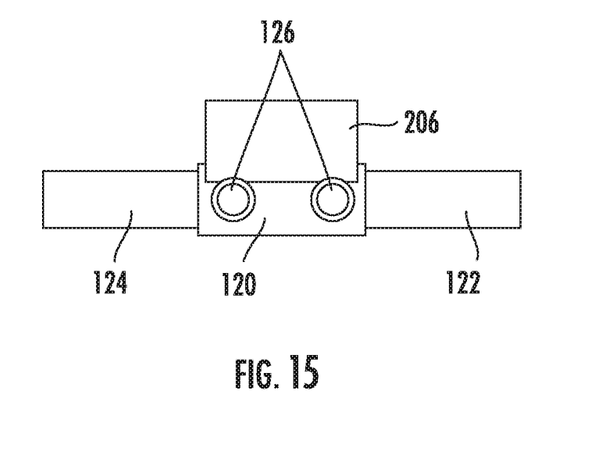
FIG. 15 is a schematic front view of the aspiration tube of the oropharyngeal airway device of FIG. 3.
Figure 16:
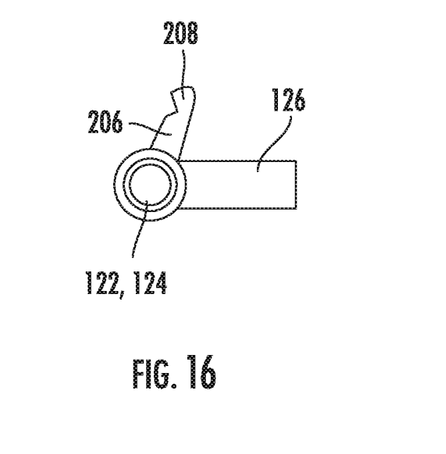
FIG. 16 is a schematic side view of the aspiration tube of the oropharyngeal airway device of FIG. 3.

The adapter 120 shown in FIGS. 15 and 16 includes the nasal prongs 126, however, in a particular aspect the adapter 120 also includes a second piece 206 extending therefrom and having a complementary retaining lip 208 configured to removably snap together with the retaining lip 204 of the fastener 200 described above with reference to FIGS. 3 and 4.

Figure 17:
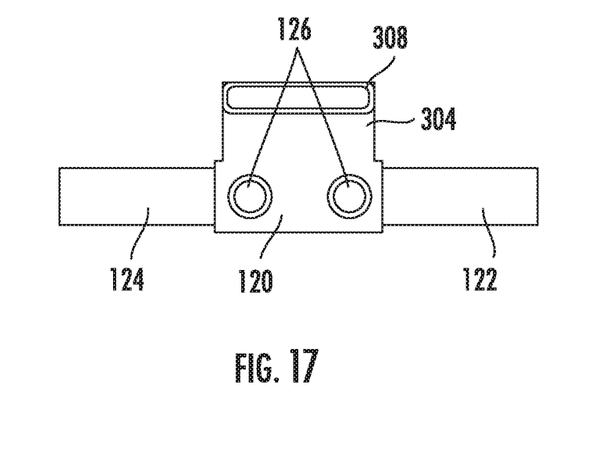
FIG. 17 is a schematic front view of the aspiration tube of the oropharyngeal airway device of FIG. 5.
Figure 18:
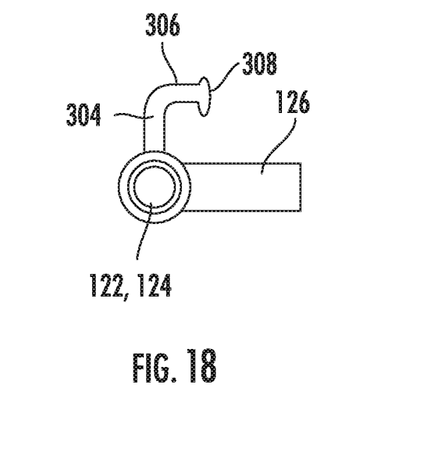
FIG. 18 is a schematic side view of the aspiration tube of the oropharyngeal airway device of FIG. 5.

Similarly, the adapter 120 shown in FIGS. 17 and 18, in another aspect, includes a first piece 304 extending in a first direction, and having a second piece 306 extending perpendicular to the first piece 304 in a second direction. A retaining lip 308 is positioned at a distal end of the second piece 306 and is configured to removably slide into the retaining slot 302 as shown in FIG. 6.

The oropharyngeal airway device 100 described herein is configured to quickly convert a typical nasal cannula to an oropharyngeal airway device 100, and vice versa.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. An oropharyngeal airway device comprising:
an elongated hollow body having a proximal opening and a distal opening;
a collar secured to the elongated hollow body around the proximal opening, the collar having an outward facing planar surface;
an adapter having a first open end and an opposing second open end, the first and second open ends are each configured to accept an aspiration tube from a nasal cannula therein in order to convert the nasal cannula for use as an oropharyngeal cannula, the adapter positioned directly over the proximal opening of the elongated hollow body and spanning across the proximal opening;
at least one fastener secured to the outward facing surface of the collar and configured to removably secure the adapter directly over the proximal opening; and
a delivery conduit coupled to the adapter and the delivery conduit positioned within the elongated hollow body in order to deliver a gas to the distal opening of the elongated hollow body and into an airway of the patient.

2. The oropharyngeal airway device of claim 1, wherein the elongated hollow body has a curved portion between the proximal end and the distal end.

3. The oropharyngeal airway device of claim 1, wherein the at least one fastener comprises a top arcuate half and a bottom arcuate half each extending from the collar towards each other and defining a slit configured for the aspiration tube to removably slide through and be secured between the top and bottom arcuate halves.

4. The oropharyngeal airway device of claim 1, wherein the at least one fastener comprises a first piece extending from the collar and having a retaining lip at a distal end of the first piece.

5. The oropharyngeal airway device of claim 4, wherein the adapter comprises a second piece extending therefrom and having a complementary retaining lip configured to removably snap together with the retaining lip of the at least one fastener.

6. The oropharyngeal airway device of claim 1, wherein the at least one fastener comprises a retaining slot within the collar.

7. The oropharyngeal airway device of claim 6, wherein the adapter comprises a first piece extending in a first direction, and having a second piece extending perpendicular to the first piece in a second direction and having a retaining lip at a distal end of the second piece configured to removably slide into the retaining slot.

8. The oropharyngeal airway device of claim 1, wherein the elongated hollow body is comprised of a rigid material.

9. The oropharyngeal airway device of claim 1, wherein the delivery conduit is in fluid communication with a gas supply.

10. The oropharyngeal airway device of claim 1, wherein the collar is configured to slide over the proximal end of the elongated hollow body.

11. An oropharyngeal airway device comprising:
an elongated hollow body having a proximal opening and a distal opening;
a collar secured to the elongated hollow body around the proximal opening, the collar having an outward facing planar surface;
an aspiration tube configured to be coupled to a gas supply;
an adapter having a first open end and an opposing second open end, the first and second open ends are each coupled to the aspiration tube, the adapted positioned directly over the proximal opening of the elongated hollow body and spanning across the proximal opening;
at least one fastener secured to the outward facing planar surface of the collar and removably securing the adapter directly over the proximal opening; and
a delivery conduit coupled to the adapter and positioned within the elongated hollow body in order to deliver gas from the gas supply to the distal opening of the elongated hollow body and into an airway of a patient.

12. The oropharyngeal airway device of claim 11, wherein the elongated hollow body has a curved portion between the proximal end and the distal end.

13. The oropharyngeal airway device of claim 11, wherein the at least one fastener comprises a top arcuate half and a bottom arcuate half each extending from the collar towards each other and defining a slit configured for the aspiration tube to removably slide through and be secured between the top and bottom arcuate halves.

14. The oropharyngeal airway device of claim 11, wherein the at least one fastener comprises a first piece extending from the collar and having a retaining lip at a distal end of the first piece.

15. The oropharyngeal airway device of claim 14, wherein the adapter comprises a second piece extending therefrom and having a complementary retaining lip configured to removably snap together with the retaining lip of the at least one fastener.

16. The oropharyngeal airway device of claim 11, wherein the at least one fastener comprises a retaining slot within the collar.

17. The oropharyngeal airway device of claim 16, wherein the adapter comprises a first piece extending in a first direction, and having a second piece extending perpendicular to the first piece in a second direction and having a retaining lip at a distal end of the second piece configured to removably slide into the retaining slot.

18. An oropharyngeal airway device comprising:
an elongated hollow body having proximal and distal ends;
a collar secured to the elongated hollow body around the proximal end, the collar having an outward facing planar surface;
an aspiration tube;
an adapter having a first open end and an opposing second open end, the first and second open ends are each coupled to the aspiration tube, the adapter positioned directly over the proximal end of the elongated hollow body and spanning across the proximal end;
a delivery conduit coupled to the adapter and positioned within the elongated hollow body in order to deliver gas to the distal end of the elongated hollow body and into an airway of a patient;
at least one fastener secured to the outward facing surface of the collar removably securing the adapter directly over the proximal opening; and
a gas supply coupled to the aspiration tube.

* * * * *